United States Patent [19]

Dopatka

[11] Patent Number: 4,545,958

[45] Date of Patent: Oct. 8, 1985

[54] MICROTITRATION PLATE

[75] Inventor: Hans-Detlef Dopatka, Marburg, Fed. Rep. of Germany

[73] Assignee: Behringwerke Aktiengesellschaft, Fed. Rep. of Germany

[21] Appl. No.: 485,831

[22] Filed: Apr. 18, 1983

[30] Foreign Application Priority Data

Apr. 19, 1982 [DE] Fed. Rep. of Germany ....... 3214317

[51] Int. Cl.[4] .......................... B01L 3/00; C12M 1/00

[52] U.S. Cl. ...................................... 422/102; 436/809

[58] Field of Search .......................... 206/563; 211/74; 356/244; 220/21, 23.8; 422/99, 102, 104; 435/293, 300, 301; 436/809

[56] References Cited

U.S. PATENT DOCUMENTS

| | | | |
|---|---|---|---|
| 3,078,020 | 2/1963 | Boonstra | 211/74 X |
| 3,356,462 | 12/1967 | Cooke et al. | 422/102 |
| 3,542,210 | 11/1970 | Sorensen | 211/74 |
| 3,713,771 | 1/1973 | Taylor et al. | 211/74 X |
| 3,992,265 | 11/1976 | Hansen | 435/300 |
| 4,252,897 | 2/1981 | Axford et al. | 435/293 X |
| 4,319,841 | 3/1982 | Suovaniemi et al. | 422/102 X |

FOREIGN PATENT DOCUMENTS

| | | | |
|---|---|---|---|
| 55-63762 | 5/1980 | Japan | 422/99 |

*Primary Examiner*—Barry S. Richman
*Assistant Examiner*—Michael S. Gzybowski
*Attorney, Agent, or Firm*—Finnegan, Henderson, Farabow, Garrett, & Dunner

[57] ABSTRACT

A microtitration plate wherein a frame and a central part are separated from one another via a continuous break and ridges are arranged at the lower face of the plate so that differences in temperature on heating between edge vessels and vessels in the central part are avoided, said differences in temperature causing the well-known "edge-effect".

7 Claims, 4 Drawing Figures

MICROTITRATION PLATE

FIELD OF THE INVENTION

The present invention relates to a microtitration plate wherein the edge and the central part are heated uniformly when said plate is placed into an incubator having a higher temperature than the plate so that a temperature gradient between reaction solutions in the edge wells and wells in the central part does not occur. The properties of said plate are, consequently, such that the so-called edge effect of conventional plates is avoided.

BACKGROUND OF THE INVENTION

This edge effect is known to be a source of errors in the Enzyme Linked Immuno Sorbent Assay (ELISA) when the latter is carried out using microtitration plates (Denmark and Chessum, Med. Lab. Sci. (1978), 35, 227). An erroneous test result is obtained which is to be seen in the fact that the color intensity in the edge wells of the microtitration plates used is increased, although a nearly identical extinction value in all wells was to be expected, based on the test arrangement employed.

This typical increase of the color intensity should not be confounded with individual deviations, the so-called outliers which seem to be distributed at random across the microtitration plate. This increase is caused by errors in the test performance, a nonhomogenous plate coating or a low quality of the plate material used.

The edge effect, on the contrary, is caused by a temperature gradient between the edge wells and the residual wells of the microtitration plate during the immunologic reaction and the enzyme reaction of the ELISA (Burt et al., J. Immunol. Meth. (1979) 31, 231).

In the case of a temperature rise by up to 1.6° C. in the edge wells, temperature-dependent steps such as the antigen-antibody binding or an enzyme reaction proceed more quickly in said wells than in the residual wells of the plate. This is demonstrated by a greater color intensity of said wells in the ELISA.

The temperature gradient between the edge wells and those in the central part is caused by more rapid heating of the plate edge. This heating may occur when the plate is placed on a support having a good heat conduction, for example the metal bottom of an incubator as well as due to the heat insulation of the central part of the plate by the air cushion below. The higher the incubation temperature and the shorter the incubation times, the more pronounced is generally said edge effect. Said edge effect may be reduced by superposing the plates and can be eliminated by floating the plates bubble-free in a warm water bath or by using appropriate heating fans.

However, both of the latter possibilities are either difficult to perform or involve much expenditure from the technical point of view (Oliver et al., J. Immunol. Meth. (1981) 42, 195).

SUMMARY OF THE INVENTION

It is an object of the present invention to provide a microtitration plate, that includes a device consisting substantially of a plate support provided with several vessels which ensures a uniform change in temperature in time of the contents of all vessels, when placed into a surrounding having a higher temperature than the plate.

It has now been found surprisingly that a temperature gradient between the edge and the central part of a microtitration plate on heating is avoided, if the plate material is shaped in adequate manner.

The present invention, which is a substantial improvement over a conventional microtitration plate, comprises changing the shape of said microtitration plate in a manner such that the capability of the edge wells of being heated is greatly reduced by means of the plate edges and that the capability of the residual plate wells of being heated is increased. Both effects coact in a manner such that the edge effect is suppressed.

To achieve the objects and in accordance with the purpose of the invention, as embodied and as broadly described herein, a microtitration plate adapted to be heated comprises a continuous frame part, a central well portion and an arrangement of ridges. The frame part includes sidewalls and an upper surface extending within the frame part and projection inwardly a predetermined distance from the sidewalls, the upper surface having an inwardly directed facing edge. The central well portion is situated within the frame part interiorly of the facing edge and includes a plurality of vessels, which are mounted on the central well portion. The facing edge and the outer surface of the well portion defines a gap between the frame part and the well portion. The arrangement of ridges includes individual ridges that are transverse support members integrally connected to diametrically opposed points on the sidewalls. The ridges are spaced longitudinally within said frame part. The ridges support the central well portion within the frame part.

Also according to the present invention, the plurality of vessels preferably is arranged in rows, each one of the rows being disposed adjacent one of the ridges, which are preferably tapered at the region of connection between the ridges and the sidewall. In addition, the sidewalls may include a base portion having a plurality of spaced indentations, which are individually positioned on the sidewalls between adjacent ridges to facilitate fluid movement through the sidewalls. Further, means are provided for heating the microtitration plates.

This is achieved according to the invention by the following shape modifications of a conventional microtitration plate illustrated in the accompanying drawings and in the descriptions referring thereto, and by similar shape modifications.

DESCRIPTION OF THE PREFERRED EMBODIMENT

Reference will now be made in detail to the presently preferred embodiment of the invention, an example of which is illustrated in the accompanying drawings.

Figure 3:
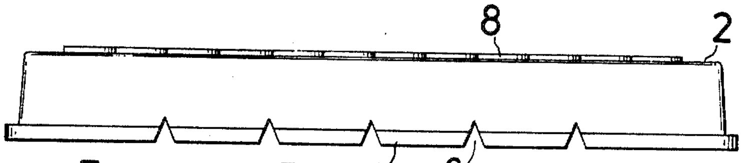
FIG. 3 is a side view of the plate of FIG. 1.
Figure 1:
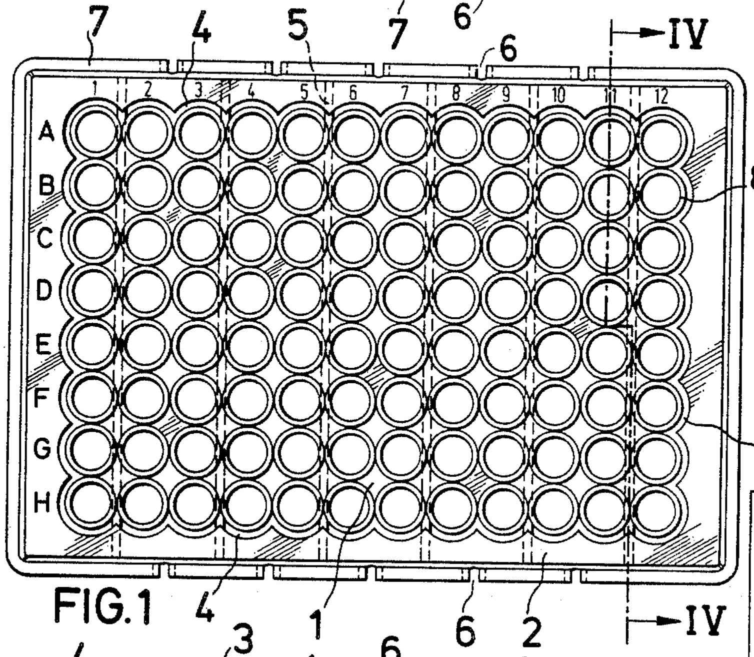
FIG. 1 is a top plan view of a microtitration plate constructed in accordance with the present invention.
Figure 4:
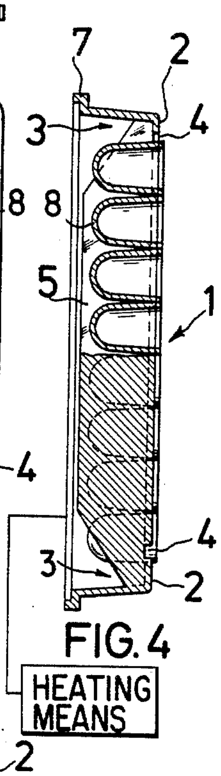
FIG. 4 is a sectional view of the plate of FIG. 1 taken along line IV—IV of FIG. 1.

The preferred embodiment of the microtitration plate is shown in FIG. 1 and is represented generally by the numeral 1. This plate includes an upper plate edge (2) of the microtitration plate, that is separated from the main part of the plate (1), except for connection points (3), which are formed by the tapered ends of ridges (5) in a manner such that a continuous break (4) is obtained.

Figure 2:
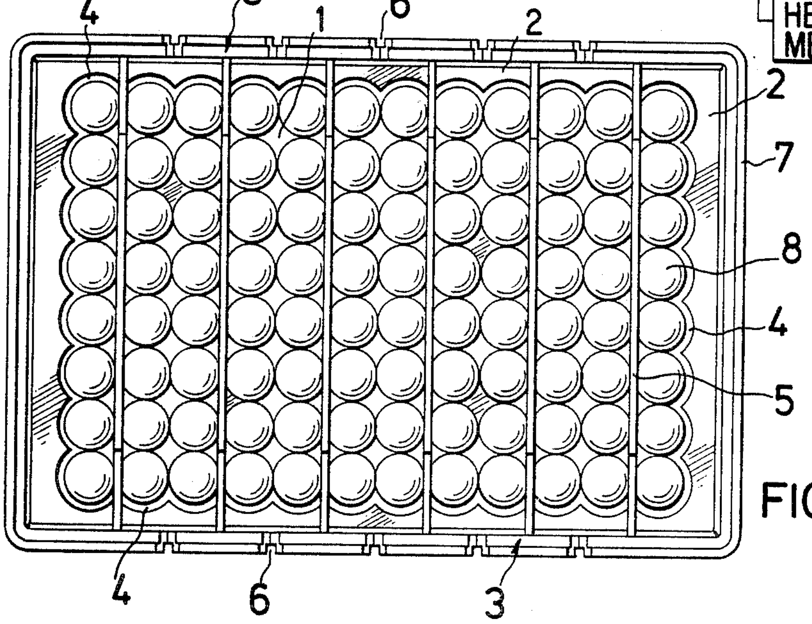
FIG. 2 is a plan view of the bottom surface of the plate of FIG. 1.

These ridges (5) are interposed vertically to the surface of the plate and are optionally constructed as high as possible without impairing the suitability for stacking several of these plates on top of each other. Between ridges (5) are positioned apertures for receiving vessels (8), which are arranged in rows. The ridges may be positioned between the first and the second, the third and the fourth, the fifth and the sixth, the seventh and the eighth, the ninth and the tenth and between the eleventh and the twelfth row of the vessels (8) as illustrated in FIGS. 1 and 2. Alternatively, the ridges (5) may be arranged vertically to the rows of vessels between the rows A to H. Further, small indentations (6) are provided at the support edge of the lower plate edge (7) in a manner such that they face each other in the interspaces between the ridges (5).

On account of break (4), the heat transfer of the rapidly heating plate edge to the edge vessels is strongly reduced. Break (4), which extends between the edge and the central part, may be enlarged to form recesses or modified so that vessels (8) and edge (2) are arranged as close as possible.

Moreover, when applying the foregoing measures, the air cushion below each plate is decreased rapidly in the case of the stacked plates (fall shaft principle for the colder air). Thus the isolated large area ridges can heat more rapidly.

When constructing ridges (5), as described herein, the heated ridges transfer the heat uniformly to the vessels adjacent in each case, heating via the ridges proceeding more rapidly than via the connection points with the plate edge. The residual influence of the plate edge is neutralized due to the fact that the ridges are tapered towards the plate edge.

Said edge effect is cancelled by the sum of the above-mentioned measures.

The microtitration plate according to the invention is stable to distortion, appropriate for automation, superposable and capable of being labelled.

It is particularly suitable for use in incubators.

What is claimed is:

1. A microtitration plate adapted to be heated, comprising:

a continuous frame part having sidewalls and an upper surface extending within said frame part and projecting inwardly a predetermined distance from said sidewalls, said upper surface having an inwardly directed facing edge;

a central well portion situated within said frame part interiorly of said facing edge and having a plurality of vessels mounted thereon, said vessels having a predetermined height and width, said facing edge and the outer surface of said well portion defining a gap between said frame part and said well portion; and an arrangement of ridges, said ridges being transverse support members integrally connected to diametrically opposed points on said sidewalls, said ridges also being spaced longitudinally within said frame part, said ridges supporting said central well portion within said frame part.

2. A microtitration plate as recited in claim 1, wherein said plurality of vessels are arranged in rows and each one of said rows is disposed adjacent one of said ridges.

3. A microtitration plate as recited in claim 1, wherein said ridges have ends that are tapered at the regions of connection between said ridges and said sidewall.

4. A microtitration plate as recited in claim 1, wherein the height of said vessels is greater than the width of said vessels.

5. A microtitration plate as recited in claim 1, including means for heating said microtitration plate.

6. A microtitration plate as recited in claim 1, wherein said sidewalls include a base portion having a plurality of spaced indentations.

7. A microtitration plate as recited in claim 6, wherein said indentations are individually positioned between adjacent ones of said longitudinally spaced ridges to facilitate fluid movement through the sidewalls.

* * * * *